(12) United States Patent
Tsao (10) Patent No.: US 8,980,304 B2
(45) Date of Patent: Mar. 17, 2015

(54) BARREL-SHAPED VAGINAL RING

(75) Inventor: Jiaxiang Tsao, Nanuet, NY (US)

(73) Assignee: Teva Women's Health, Inc., Woodcliff Lake, NJ (US)

( * ) Notice: Subject to any disclaimer, the term of this patent is extended or adjusted under 35 U.S.C. 154(b) by 29 days.

(21) Appl. No.: 13/818,044

(22) PCT Filed: Aug. 18, 2011

(86) PCT No.: PCT/US2011/048183
§ 371 (c)(1),
(2), (4) Date: Jul. 8, 2013

(87) PCT Pub. No.: WO2012/024461
PCT Pub. Date: Feb. 23, 2012

(65) Prior Publication Data
US 2013/0269706 A1    Oct. 17, 2013

Related U.S. Application Data

(60) Provisional application No. 61/375,719, filed on Aug. 20, 2010.

(51) Int. Cl.
| | |
|---|---|
| *A61F 6/06* | (2006.01) |
| *A61F 6/14* | (2006.01) |
| *A61K 9/00* | (2006.01) |
| *A61K 31/167* | (2006.01) |
| *A61K 31/216* | (2006.01) |
| *A61K 31/565* | (2006.01) |
| *A61K 31/569* | (2006.01) |
| *A61K 31/58* | (2006.01) |

(52) U.S. Cl.
CPC .............. *A61F 6/142* (2013.01); *A61K 9/0036* (2013.01); *A61K 31/167* (2013.01); *A61K 31/216* (2013.01); *A61K 31/565* (2013.01); *A61K 31/569* (2013.01); *A61K 31/58* (2013.01)
USPC ........................................... 424/430

(58) Field of Classification Search
None
See application file for complete search history.

(56) References Cited

U.S. PATENT DOCUMENTS

| | | | |
|---|---|---|---|
| 4,012,496 | A | 3/1977 | Schopflin et al. |
| 6,126,958 | A | 10/2000 | Saleh et al. |
| 6,264,973 | B1 | 7/2001 | Mahashabde et al. |
| 2002/0090390 | A1* | 7/2002 | Mahashabde et al. ........ 424/425 |
| 2009/0004246 | A1 | 1/2009 | Woolfson et al. |

OTHER PUBLICATIONS

The International Search Report and the Written Opinion for International Application PCT/US2011/048183, mailed Dec. 19, 2011.

* cited by examiner

*Primary Examiner* — Anand Desai
*Assistant Examiner* — Melissa Mercier
(74) *Attorney, Agent, or Firm* — Fanelli Haag & Kilger PLLC (57) ABSTRACT

The present invention relates to annular intravaginal devices comprising an aperture, methods of making, and uses thereof. The annular devices comprise an aperture extending into the device, the aperture having: (a) an interior diameter, and (b) an exterior entry diameter, wherein the exterior entry diameter of the aperture is less than the interior diameter of the aperture.

4 Claims, 7 Drawing Sheets

BARREL-SHAPED VAGINAL RING

FIELD OF THE INVENTION

The present invention relates to annular intravaginal devices comprising an aperture, methods of making, and uses thereof. The annular intravaginal devices comprise an aperture extending into the device, the aperture having: (a) an interior diameter, and (b) an exterior entry diameter, wherein the exterior entry diameter of the aperture is less than the interior diameter of the aperture.

BACKGROUND OF THE INVENTION intravaginal devices can be used to vaginally administer an active agent to a female subject. Various benefits are associated with vaginal delivery of active agents. For example, intravaginal delivery can provide administration of the active agent to a subject while avoiding the first-pass effect in the liver. Active agents administered intravaginally can directly diffuse through the vaginal tissues to provide local or systemic effects. The ability to provide a local or systemic effect allows intravaginal delivery to treat numerous conditions within and outside the vaginal and/or urogenital tract such as hormonal dysfunctions, inflammation, infection, pain, and incontinence. As a result, intravaginal delivery has been considered an efficacious method for administering various active agents.

Several methods for delivering an active agent intravaginally exist in the art, such as for example, the use of intravaginal rings, intrauterine devices, and intravaginal pessaries. See e.g., U.S. Pat. Nos. 4,823,814; 4,607,630; 4,553,972; 4,286,587; and 4,249,531. Of these methods, intravaginal rings provide a versatile, comfortable method for delivering active agents which can be readily inserted and removed.

There is a need in the art for improved intravaginal devices capable of delivering active agents to the vaginal and/or urogenital tract, with the devices having increased physical integrity, safety, and comfort.

BRIEF SUMMARY OF THE INVENTION

The present invention is directed to an annular intravaginal device, the device comprising an aperture extending into the device, the aperture having: (a) an interior diameter, and (b) an exterior entry diameter, wherein the exterior entry diameter of the aperture is less than the interior diameter of the aperture.

The present invention is also directed to a method of making an annular intravaginal device, the method comprising: (a) forming the intravaginal device by molding or compressing a device matrix in a mold, wherein an aperture is formed simultaneously with the molding or compressing of the device matrix, the aperture extending into the device and having: (i) an interior diameter, and (ii) an exterior entry diameter, wherein the exterior entry diameter of the aperture is less than the interior diameter of the aperture, and (b) placing an aperture matrix inside the aperture of the device matrix. In some embodiments, the aperture matrix is in a non-solid state when placed in the aperture, and then solidifies after placement in the aperture. The present invention is also directed to an intravaginal device made by this method.

In some embodiments, the aperture extends completely through the device, thereby forming a first exterior entry diameter, an interior diameter and a second exterior entry diameter. In some embodiments, the second exterior entry diameter of the aperture is equal to the first exterior entry diameter of the aperture. In some embodiments, the second exterior entry diameter of the aperture is greater than the first exterior entry diameter of the aperture. In some embodiments, the second exterior entry diameter of the aperture is less than the first exterior entry diameter of the aperture.

In some embodiments, the device comprises two to twenty apertures. In some embodiments, the device comprises eight to fifteen apertures.

In some embodiments, the device comprises an aperture matrix contained within the aperture. In some embodiments, the aperture matrix comprises an active agent. In some embodiments, the active agent is a steroid hormone, an anticholinergic, an anesthetic, or combinations thereof. In some embodiments, the active agent is oxybutynin, lidocaine, danazol, etonogestrel, ethinyl estradiol, or combinations thereof.

In some embodiments, a cap covers the aperture matrix.

In some embodiments, the interior diameter of the aperture is about 4 mm to about 8 mm. In some embodiments, the exterior entry diameter of the aperture is about 3 mm to about 6 mm.

In some embodiments, the exterior entry diameter of the aperture is about 20% smaller than the interior diameter of the aperture. In some embodiments, the exterior entry diameter of the aperture is about 50% smaller than the interior diameter of the aperture.

In some embodiments, the device comprises an organosiloxane polymer, plastic, thermoplastic, thermoset plastic, or combinations thereof. In some embodiments, the organosiloxane polymer is a polysiloxane. In some embodiments, the polysiloxane selected from the group consisting of a methyl polysiloxane, methyldimethyl polysiloxane, ethylpolysiloxane, propylpolysiloxane, trifluoropropyl-methyldimethyl polysiloxane, and combinations thereof.

In some embodiments, the plastic comprises a polysiloxane, a polyalkylene, a polystyrene, a polyvinyl acetate, a polyvinyl chloride, a polyester, a polyurethane, an acrylic, a nylon, a dacron, a teflon, or combinations thereof.

In some embodiments, the device has an outer diameter of about 30 mm to about 90 mm. In some embodiments, the device has a cross-sectional diameter of about 2 mm to about 20 mm.

In some embodiments, the invention is directed to a method of contraception comprising administering to a female an intravaginal device comprising: (a) an aperture extending into the device, the aperture having: (i) an interior diameter; and (ii) an exterior entry diameter, wherein the exterior entry diameter of the aperture is less than the interior diameter of the aperture, and (b) an aperture matrix contained within the aperture, wherein the aperture matrix comprises an estrogen and a progestin in an amount sufficient to provide contraception.

In some embodiments, the invention is directed to a method of hormone replacement therapy comprising administering to a female an intravaginal device comprising: (a) an aperture extending into the device, the aperture having: (i) an interior diameter; and (ii) an exterior entry diameter, wherein the exterior entry diameter of the aperture is less than the interior diameter of the aperture, and (b) an aperture matrix contained within the aperture, wherein the aperture matrix comprises an estrogen in an amount sufficient to provide relief from symptoms associated with menopause or peri-menopause.

In scene embodiments, the invention is directed to a method for anesthetizing the cervical region of a female, the method comprising: (a) administering to the vaginal canal of a female an intravaginal device comprising: (i) an aperture extending into the device, the aperture having: (1) an interior diameter; and (2) an exterior entry diameter, wherein the exterior entry diameter of the aperture is less than the interior diameter of the aperture, and, (ii) an aperture matrix contained within the aperture, wherein the aperture matrix comprises an anesthetic in an amount sufficient to anesthetize the cervical region, and (b) removing the intravaginal ring from the vaginal canal after induction of the anesthesia of the cervical region.

In some embodiments, the invention is directed to a method of treating osteoporosis, the method comprising administering to a female an intravaginal device comprising: (a) an aperture extending into the device, the aperture having: (i) an interior diameter; and (ii) an exterior entry diameter, wherein the exterior entry diameter of the aperture is less than the interior diameter of the aperture, and (b) an aperture matrix contained within the aperture, wherein the aperture matrix comprises an estrogen in an amount sufficient to provide relief from symptoms associated with osteoporosis.

In some embodiments, the invention is directed to a method of treating urinary incontinence, the method comprising administering to a female an intravaginal device comprising: (a) an aperture extending into the device, the aperture having: (i) an interior diameter; and (ii) an exterior entry diameter, wherein the exterior entry diameter of the aperture is less than the interior diameter of the aperture, and (b) an aperture matrix contained within the aperture, wherein the aperture matrix comprises an anticholinergic in an amount sufficient to provide relief from symptoms associated with urinary incontinence.

DETAILED DESCRIPTION OF THE INVENTION

The present invention relates to annular intravaginal devices comprising an aperture, methods of making, and uses thereof.

Throughout the present disclosure, all expressions of percentage, ratio, and the like are "by weight" unless otherwise indicated. As used herein, "by weight" is synonymous with the term "by mass," and indicates that a ratio or percentage defined herein is done according to weight rather than volume, thickness, or some other measure.

As used herein, the term "about," when used in conjunction with a percentage or other numerical amount, means plus or minus 10% of that percentage or other numerical amount. For example, the term "about 80%," would encompass 80% plus or minus 8%.

Intravaginal Devices

The present invention is directed to an annular intravaginal device comprising an aperture extending into the device, the aperture having: (a) an interior diameter, and (b) an exterior entry diameter, wherein the exterior entry diameter of the aperture is less than the interior diameter of the aperture.

As used herein, an "intravaginal device" refers to an object suitable in size, shape and composition for placement in the vaginal and/or urogenital tract of a female, including, e.g., the vagina, cervix, or uterus of a female. In some embodiments, the term intravaginal device can also refer to a device suitable administration of an active agent, e.g., a drug, to a female.

The device of the present invention is annular in shape. As used herein, "annular" refers to a shape of, relating to, or forming a ring. Annular shapes suitable for use with the present invention include a ring, an oval, an ellipse, a toroid, and the like. In some embodiments, the intravaginal device of the present invention is a vaginal ring. The shape of the intravaginal device of the present invention can be pliable or malleable, and can be altered or deformed temporarily, i.e., can temporarily assume a non-annular shape, e.g., when being inserted into a female. In some embodiments, the device is elastic, i.e., the device spontaneously returns to its original shape after being deformed. In some embodiments, the device can be flexible. As used herein, "flexible" refers to the ability of a solid or semi-solid to bend or withstand stress and strain without being damaged or broken. For example, the device of the present invention can be deformed or flexed, such as, for example, using finger pressure (e.g., applying pressure from opposite external sides of the device using the fingers), and upon removal of the pressure, return to its original shape. The flexible properties of the intravaginal device of the present invention can be useful for enhancing user comfort, and also for ease of administration to the vaginal tract and/or removal of the device from the vaginal tract.

The intravaginal device of the present invention comprises one or more apertures. As used herein, an "aperture" refers to any cavity, hole, depression, indentation, or recess extending from the surface into the device which has the characteristics described herein.

While not being bound by any particular theory, the inventors have found that the intravaginal devices described herein achieve numerous benefits over previous intravaginal devices. For example, the intravaginal devices described herein can be used as a standardized template, which can be interchanged and used in conjunction with various second matrices, e.g. aperture matrices, for administering various types of drugs, achieving various release rates, and holding various dosage amounts.

In some embodiments, the intravaginal device of the present invention is used as a template containing no active agent. The intravaginal device has one or more apertures, the apertures capable of being filled with the desired active agent. In some embodiments, the aperture of the device template is filled with a matrix containing active agent. The dosage amount of the active agent in the intravaginal device can modified by varying the amount of active agent inserted into an aperture, varying the concentration of the active agent in the aperture matrix, varying the aperture matrix composition and/or varying the number of apertures which are filled in the intravaginal device. Take, for example, an intravaginal device having 10 apertures, each aperture capable of holding an aperture matrix comprising 1 unit of active agent. If the desired dosage amount of active agent is 4 units, then 4 apertures of the intravaginal device can be filled with the matrix having the active agent, and the remaining 6 apertures can remain unfilled, or can be filled with a matrix comprising no active agent. If 8 units of active agent are desired, then 8 apertures can be filled with the matrix having the active agent, and the remaining 2 apertures can remain unfilled, or can be filled with a matrix comprising no active agent.

In some embodiments, more than one active agent can be administered from the same intravaginal device. For example, the intravaginal device of the present invention can comprise 2 or more apertures, the first active agent can be inserted into one or more apertures, and a second active agent can be inserted into one or more separate apertures. As described above, the dosage amount of each active agent can be adjusted depending on the need of the subject to which the device is administered.

The shape of the apertures can provide various benefits. For example, in the intravaginal device of the present invention, the exterior diameter is less than the interior diameter of the aperture. This shape allows for minimized exposure of the aperture matrix (the matrix containing the active agent) to the external environment. In some embodiments, minimized direct exposure of the aperture matrix to the external environment (e.g., the endothelial lining of the vaginal tract) can reduce side effects associated with vaginal delivery of active agents, e.g., irritation and/or inflammation.

One problem associated with some previous vaginal rings, e.g., reservoir and/or matrix rings, is that substantial passive diffusion of the active agent can occur from the reservoir or matrix to the external environment during storage of the device. This diffusion can result in a loss of active agent as the active agent diffuses out of the device, resulting in inconsistent dosage amounts once the device is administered to a female. Passive diffusion can also result in an increased concentration of active agent on the outside surface of the device. The increased concentration on the outside of the device can result in a "burst effect" upon administration to a female, i.e., a rapid delivery of active agent to the female upon the initial administration of the device to the female, resulting from the increased concentration of the active agent on the outside of the device. In the present invention, direct exposure of the aperture matrix containing the active agent to the external environment can be reduced relative to a traditional reservoir or matrix ring, since the aperture matrix has a relatively small surface area relative to the remainder of the device. Thus, in some embodiments the amount of diffusion of active agent from the aperture matrix to the outside of the device prior to administration is also reduced. Therefore, in some embodiments, the device of the present invention provides an intravaginal device having reduced burst effect relative to traditional matrix and/or reservoir rings, or vaginal rings containing cylindrical apertures.

Additionally, by minimizing the exterior entry diameter (by which the aperture matrix is exposed) relative to the interior diameter, increased amounts of active agent can be present in the device while not increasing exposure of the aperture matrix to the environment, relative to a vaginal ring simply having cylindrical apertures.

The shape of the aperture can be adjusted to provide a desired release rate. In some embodiments, as the exterior entry diameter of the aperture is reduced, the release rate of the active agent from the device is reduced. Since the interior diameter of the aperture is larger than the exterior entry diameter of the aperture, the dosage amount can remain the same, but the release rate can be reduced. Thus, the shape of the aperture can be used to alter the release rate, without altering the dosage amount of active agent, the matrix of the device composition, or the aperture matrix composition.

In some embodiments, the shape of the aperture can increase the physical containment of the aperture matrix in the aperture of the device. By way of example, since the interior diameter of the aperture is greater than the exterior entry diameter of the aperture, the size of the interior of the aperture matrix is to large to fit through the exterior opening of the aperture. Thus, the aperture matrix cannot be removed from the intravaginal device without disrupting or otherwise deforming the device matrix and/or the aperture matrix. Thus, the shape of the aperture provides a means for securing the aperture matrix in the intravaginal device without the need for an adhesive, or a bonding interaction between the aperture matrix and the matrix of the intravaginal device, in some embodiments, the shape of the aperture is of great benefit, since the intravaginal device must be temporarily deformed, i.e., bent, when administering the device to a female, which can result in the aperture matrix being expelled form the intravaginal device if the aperture matrix is not sufficiently secured to the device. The shape of the aperture provides the physical integrity to keep the aperture matrix inside the intravaginal device even when the intravaginal device is deformed.

In some embodiments, during manufacturing, the aperture matrix is placed inside the aperture of the intravaginal device when the aperture matrix is in a non-solid physical state, i.e., in a liquid or semi-solid state. The aperture matrix then solidifies and/or polymerizes. During the solidification and/or polymerization, the aperture matrix may expand or contract in size. If the aperture matrix contracts in size, then the shape of the aperture with the exterior entry diameter less than the interior diameter) provides physical support to retain the aperture matrix inside the intravaginal device.

Figure 6A:
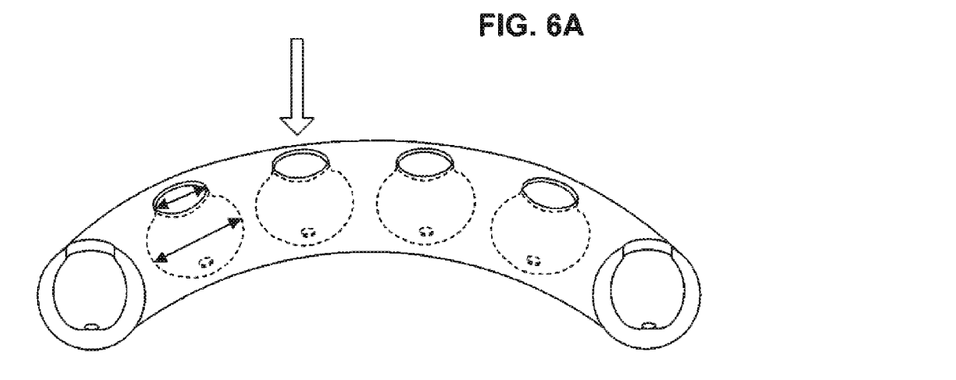
FIG. 6A depicts the vertical orientation of the apertures in a bi-sectioned intravaginal device, the arrow showing the vertical orientation of the apertures.
Figure 6B:
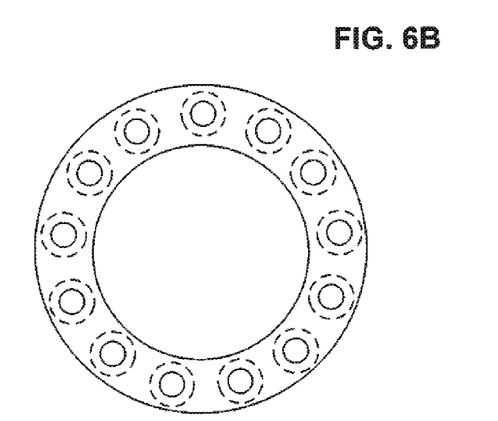
FIG. 6B is a top view of the entire intravaginal ring showing the vertical orientation of the apertures in the device.

The aperture can be located at various orientations on the annular intravaginal device. For example, in some embodiments, the aperture extends vertically into the device, i.e., if the device is placed flat on a surface, the aperture extends vertically from the top of the device into the interior of the device towards the bottom of the device, and perpendicularly to the remainder of the device. An example of a "vertical" orientation of an aperture is demonstrated in FIG. 6A, wherein the arrow indicates the vertical orientation of an aperture in a device. In some embodiments, an intravaginal device having an aperture extending vertically into the device provides a more convenient method of manufacturing, since the intravaginal device can be placed horizontally on a flat surface, and the aperture matrix can be placed inside the aperture of the intravaginal device. In some embodiments, the aperture matrix is in a liquid or semi-solid state, and can be inserted into the aperture, and then allowed to solidify/polymerizes, without leaking or falling out of the aperture. In some embodiments wherein the device comprises an aperture extending vertically into the device, the aperture matrix has reduced (or no) direct contact with the vaginal endothelium when administered to a female due to the orientation of the aperture on the intravaginal device when the device is placed in a vaginal tract of a female. The reduced direct contact can result in reduced inflammation, reduced irritation or other undesirable side effects associated with direct physical contact between the vaginal endothelium and the aperture matrix and/or the active agent in the aperture matrix.

Figure 7A:
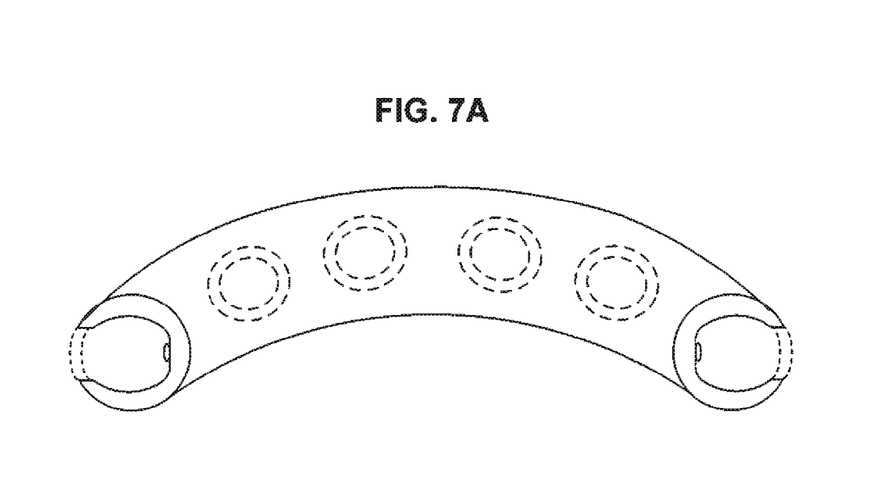
FIG. 7A depicts the horizontal orientation of the apertures in a bi-sectioned intravaginal device, the arrow showing the horizontal orientation of the apertures.
Figure 7B:
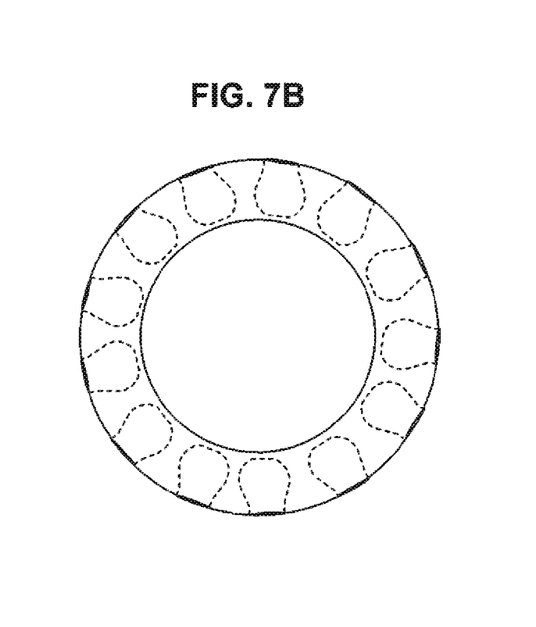
FIG. 7B is a top view of the intravaginal device showing the horizontal orientation of the apertures in the device.

In some embodiments, the apertures can be oriented such that they extend horizontally into the device. See, FIG. 7A. Various other orientations, or combinations of angles of orientations, of the apertures in the device can be used.

Figure 1A:
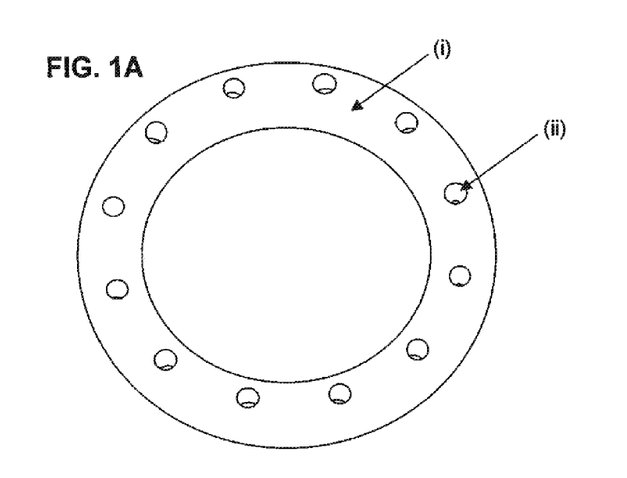
FIG. 1A depicts a top-down view of a vaginal ring having: (i) a silicone polymer matrix, and (ii) apertures extending vertically into the matrix.
Figure 1B:
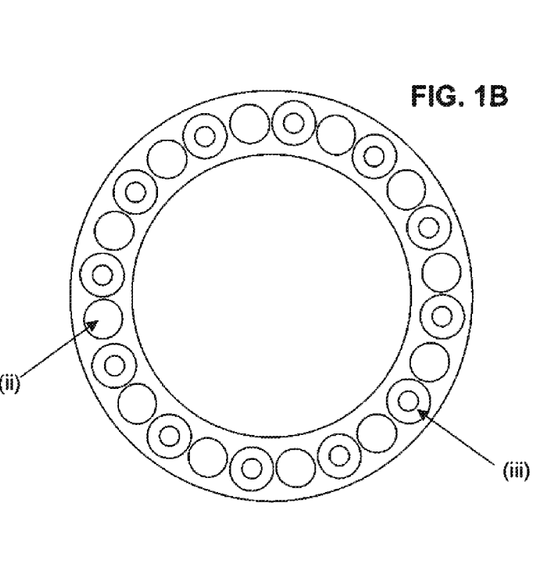
FIG. 1B depicts a bottom-up view of a vaginal ring having; (ii) apertures extending vertically into the matrix, and (iii) ejector pin pads in between the apertures.
Figure 1C:
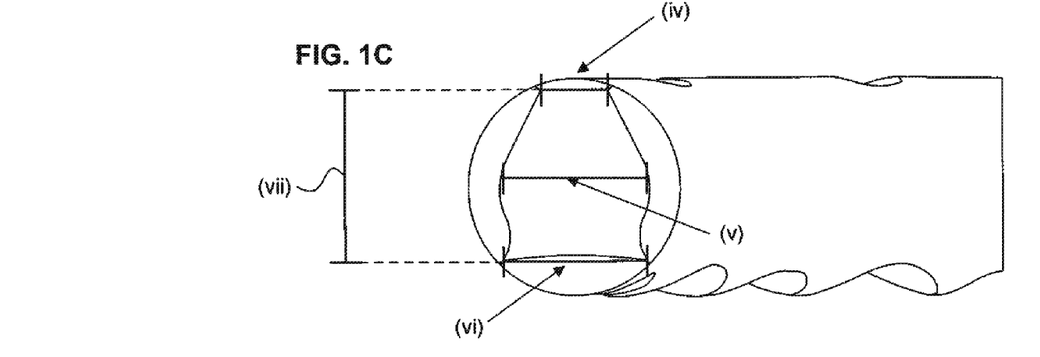
FIG. 1C depicts a cross-sectional view of a vaginal ring aperture having: (iv) a first exterior entry diameter, (v) an interior diameter, and (vi) a second exterior entry diameter. Also noted is the aperture length (vii).
Figure 3:
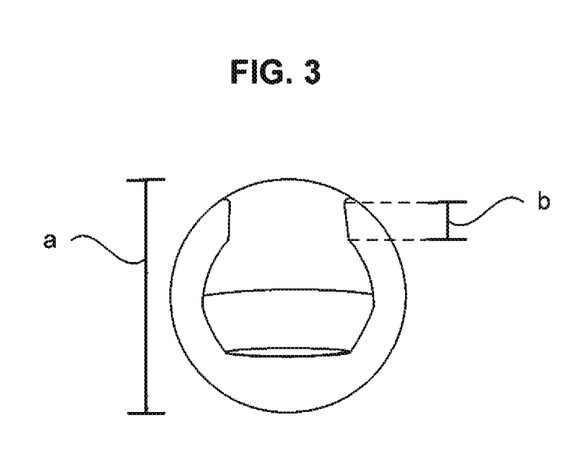
FIG. 3 depicts an exemplary cross-sectional view of a vaginal ring, the ring having (a) a cross-sectional diameter and (b) a exterior entry neck on the first exterior opening.
Figure 4:
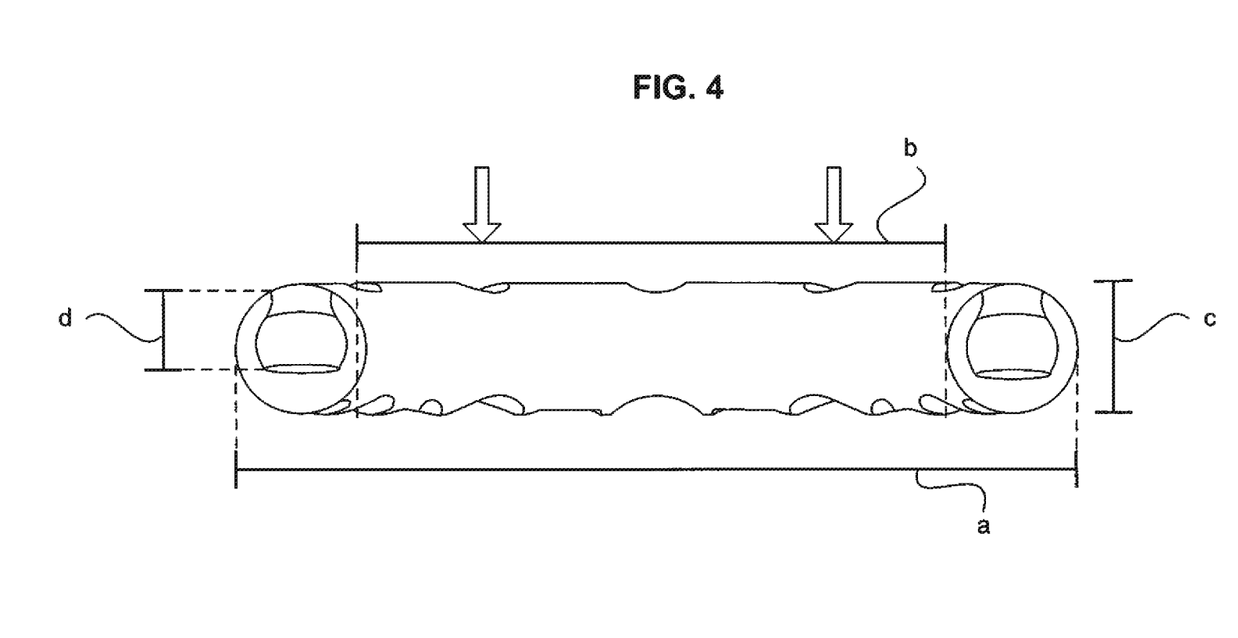
FIG. 4 depicts a cross-sectional view of a bisected vaginal ring cut vertically. The device has (a) an outer diameter, (b) an inner diameter, and (c) a cross-sectional diameter. The arrows indicate the vertical orientation of the apertures in the intravaginal ring. The length of the aperture (d) is also identified.

The aperture of the present invention forms a void in the device. The aperture has an exterior entry having a diameter (FIG. 1C(iv)), an interior having a diameter (FIG. 1C(v)), and an aperture length (FIG. 1C(vi)). In some embodiments, the exterior entry has a neck, the thickness of which can vary (FIG. 3(b)). In some embodiments, the exterior entry can be beveled.

As used herein, "diameter" refers to the distance across the cross-section of the aperture that passes through the midpoint of the cross-section of the aperture. In some embodiments, the cross-section can be of an irregular shape. Thus, in some embodiments, the diameter is the average diameter of the irregular cross-sectional shape. In some embodiments, the diameter is the longest straight line segment that passes through the midpoint of the cross-section of the aperture.

Figure 2:
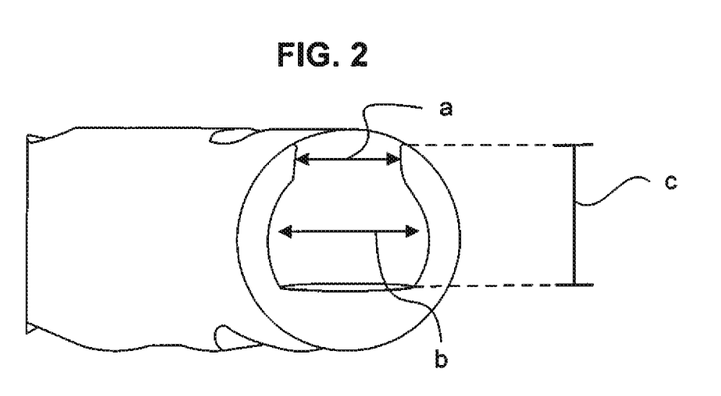
FIG. 2 depicts an exemplary cross-sectional view of a vaginal ring aperture having (a) a first exterior entry diameter, (b) an interior diameter, and (c) a length.

As used herein, the "exterior entry diameter" refers to the diameter of the external entry of the aperture, i.e., the portion of the aperture exposed to the external environment, e.g., the vagina, uterus, or cervix. See, e.g., FIG. 2(a). In some embodiments, the external entry has a "neck." FIG. 3(b). The neck can have various thicknesses, from, e.g., 0.2 mm to 3 mm, 0.5 to 2.5 mm, 0.8 mm to 2.0 mm, or 1.0 mm to 1.5 mm. In some embodiments, the neck is beveled, such that the diameter of the outside of the neck is larger than the diameter of the inside of the neck. When the exterior entry is beveled, then the exterior entry diameter refers to the minimum diameter along the exterior entry neck.

As used herein, "interior diameter" refers to a portion of an aperture that is contained within the intravaginal device that is not exposed to the outside environment, e.g., the vagina, uterus, or cervix. In some embodiments, "interior diameter" refers to the maximum diameter in the interior of the aperture. In some embodiments, the interior diameter is the diameter of the cross-section of the aperture, at the midpoint on the length of the aperture.

In the present invention, the interior diameter is greater than the exterior entry diameter. In some embodiments, the interior diameter of the aperture is about 2 mm to about 10 mm, about 3 mm to about 9 mm, about 4 mm to about 8 mm, or about 5 mm to about 7 mm. In some embodiments, the interior diameter of the aperture is about 4 mm to about 8 mm. In some embodiments, the interior diameter of the aperture is about 3 mm, about 4 mm, about 5 mm, about 6 mm, or about 7 mm.

In some embodiments, the exterior entry diameter of the aperture is about 1 mm to about 8 mm, about 2 mm to about 7 mm, about 3 mm to about 6 mm, or about 4 mm to about 5 mm. In some embodiments, the exterior entry diameter of the aperture is about 3 mm to about 6 mm. In some embodiments, the exterior entry diameter of the aperture is about 2 mm, about 3 mm, about 4 mm, about 5 mm, or about 6 mm.

In some embodiments, the exterior entry diameter of the aperture is about 60% smaller than the interior diameter, or about 50% smaller or about 40% smaller, or about 30% smaller, or about 20% smaller, or about 10% smaller than the interior diameter. In some embodiments, the exterior entry diameter of the aperture is about 20% smaller than the interior diameter. In some embodiments, the exterior entry diameter of the aperture is about 50% smaller than the interior diameter.

The aperture can be of various shapes. In some embodiments, the shape of a cross-section of the aperture (e.g., the exterior entry cross-section or an interior cross-section) can be, but is not limited to, an amorphous shape, substantially circular, substantially oval, substantially in the form of a polygon (e.g., triangular, rectangular, pentangular, etc.) or combinations thereof. In some embodiments, the shape of the cross-section of the aperture is circular or oval.

The length of the aperture can vary. The length (or depth) of the aperture is depicted in FIG. 2(c). In some embodiments, the length of the aperture is about 2 mm to about 15 mm, about 3 mm to about 10 mm, about 4 mm to about 8 mm. In some embodiments, the length of the aperture extends completely through the device, thereby forming a second exterior entry on the opposing side of the device. In some embodiments, the second exterior entry diameter is equal to the first exterior entry diameter. In some embodiments, the second exterior entry diameter is greater than the first exterior entry diameter. In some embodiments, the second exterior entry diameter is less than the first exterior entry diameter.

More than one aperture can be present in the device of the invention. In some embodiments, the device comprises one to fifty, two to twenty-five, three to twenty, five to eighteen, four to seventeen, three to thirteen, eight to fourteen or nine to twelve apertures. In some embodiments, the device comprises three to twenty apertures. In some embodiments, the device comprises eight to fifteen apertures. In some embodiments, the device comprises twelve apertures. In some embodiments, the device comprises thirteen apertures. In some embodiments, the device comprises fourteen apertures. In some embodiments, the device comprises fifteen apertures.

Apertures having various volumes can be used in the present invention. In devices having more than one aperture, each aperture can have the same or different volumes on the same device. For example, in some embodiments, the intravaginal device can contain more than one aperture, wherein the volume of each aperture is equivalent to the other apertures on the device. Alternatively, in some embodiments, the intravaginal device can contain more than one aperture, wherein the volume of a first aperture is different from the volume of a second or subsequent apertures. The variation in aperture volume can be used to facilitate the delivery of different amounts of active agent to a subject.

In some embodiments, the volume of the aperture can be 20 $mm^3$ to 1500 $mm^3$, 50 $mm^3$ to 1000 $mm^3$, 60 $mm^3$ to 800 $mm^3$, 80 $mm^3$ to 600 $mm^3$, 100 $mm^3$ to 500 $mm^3$, or 150 $mm^3$ to 400 $mm^3$.

In some embodiments, the intravaginal device of the present invention comprises a device material (i.e., a device matrix) and optionally an aperture matrix. As used herein, a "matrix" refers to any solid, semi-solid, or gel medium. In some embodiments, the matrix is compatible with and suitable for dispersion of an active agent. In some embodiments, the matrix can be chosen due to its mechanical and physical properties (e.g., solubility of an active agent in the matrix). The matrix of the intravaginal device can be a homogeneous matrix, or a heterogeneous matrix. In some embodiments, the device can have more than one matrix.

Materials used in the intravaginal device of the present invention are suitable for placement in the vaginal tract, i.e., they are nontoxic and can further be non-absorbable in the subject. In some embodiments, the matrix is compatible with an active agent, i.e., the matrix does not chemically react with the active agent to chemically change either the active agent or the materials used in the intravaginal device. In some embodiments, the matrix is non-permeable to an active agent, e.g., the active agent is impermeable to the device matrix. In some embodiments, the matrix is permeable to the active agent, and is used to alter the release rate of the active agent from the vaginal device. In some embodiments, the matrix can be capable of being suitably shaped for intravaginal administration. The matrix can include an organosiloxane polymer. In some embodiments, the organosiloxane polymer is a polysiloxane. In some embodiments, the polysiloxane is selected from the group consisting of a methyl polysiloxane, methyldimethyl polysiloxane, ethylpolysiloxane, propylpolysiloxane, trifluoropropyl-methyldimethyl polysiloxane, and combinations thereof.

The matrix can include a plastic. As used herein, a "plastic" refers to any of numerous organic synthetic or processed thermoplastic or thermosetting polymers. Suitable plastic polymers include, but are not limited to, the polyhydroxy acids poly(lactic acid) (PLA), poly(glycolic acid) (PGA), poly(lactides-co-glycolides) (PLGA), poly(DL-lactide-e-caprolactone), and polyurethane polymers. In some embodiments, the plastic can be a polyalkylene, a polystyrene, a polyvinyl acetate, a polyvinyl chloride, a polyester, a polyurethane, an acrylic, a nylon, a dacron, a teflon, or combinations thereof.

In some embodiments, the plastic of the matrix can be a thermoplastic or a thermoset plastic. As used herein, a "thermoplastic polymer" is a polymer capable of being softened by heating and hardened by cooling through a temperature range characteristic of the polymer. In the softened state, thermoplastic polymers can be shaped by flow, molding or extrusion. Suitable thermoplastic polymer materials are known to those in the art, e.g. a thermoplastic olefin blend, nylon, polyethylene, polypropylene, polyvinyl acetate (PVA), polyvinyl chloride (PVC), polystyrene, teflon, acrylic, ethylene-vinylacetate copolymers, and styrene-butadiene-styrene copolymers.

Thermoplastic elastomeric polymers can be used in the matrix of the present invention. As used herein, "thermoplastic elastomeric polymers" include any material that possesses elasticity and resilience at ambient temperatures, without the need for vulcanization to develop rubberlike elasticity. Suitable thermoplastic elastomeric materials include, but are not limited to, polyurethanes, polyesters, polyalkylenes, and combinations thereof. In some embodiments, the thermoplastic elastomeric material can be, but is not limited to, a thermoplastic olefin blend. In some embodiments, the thermoplastic elastomeric material is a styrene-ethylene-butylene modified block copolymer.

In some embodiments of the invention, the matrix comprises a thermoset plastic polymer. As used herein, a "thermoset plastic polymer" is any material that is shaped irreversibly under the influence of heat through the formation of a covalently linked, thermally stable network. Suitable thermoset plastic materials include, but are not limited to, crosslinked polymers, copolymers, block copolymers, and combinations thereof.

In some embodiments of the invention, the polymer material is an elastomer, e.g., a thermosetting elastomer, including, e.g., a silicone co-polymer (thermosetting type). As used herein, an "elastomer" refers to an amorphous polymer network formed when a polymer or a mixture of polymers undergo cross-linking. Each polymer is comprised of monomeric units, which are linked together to form the polymer. The monomeric units can comprise carbon, hydrogen, oxygen, silicon, halogen and combinations thereof. For example, the intravaginal device of the present invention can be produced using silicone polymers which may include various catalysts or cross-linking agents. Such silicone compounds, catalysts and crosslinking agents are known in the art, see e.g., U.S. Pat. No. 4,888,074. A silicone composition can include any organo-silicone compound capable of crosslinking, with or without the presence of crosslinking agents. Examples include, but are not limited to, polysiloxane and derivative thereof.

In some embodiments, the matrix comprises a polysiloxane, a polyalkyene, a polystyrene, a polyvinyl acetate, a polyvinyl chloride, a polyester, a polyurethane, an acrylic, a nylon, a dacron, a teflon, or combinations thereof.

In some embodiments, the matrix is a polysiloxane, an ethylene-vinylacetate copolymer, or combinations thereof.

In some embodiments, the matrix of the intravaginal device comprises of polysiloxane. As used herein, a "polysiloxane" refers to any of various compounds containing alternate silicon and oxygen atoms in either a linear or cyclic arrangement usually with one or two organic groups attached to each silicon atom. For example, polysiloxanes include substituted polysiloxanes, and diorganopolysiloxanes such as diarylpolysiloxanes and dialkylpolysiloxanes. In some embodiments, the polysiloxane comprises a siloxane unit as illustrated in Formula 1, Formula I wherein X can be 1 to 200, Y can be 1 to 200 and Z can be 1 to 300, and wherein $R_1$, $R_2$, $R_3$, $R_4$ and $R_5$ can be independently selected from the group consisting of $(C_{1-6})$alkyl, amino$(C_{1-6})$alkyl, hydroxy$(C_{1-6})$alkyl, haloalkyl, cyano$(C_{1-6})$alkyl, thio$(C_{1-6})$alkyl, carboxy$(C_{1-6})$alkyl, aryl$(C_{1-6})$alkyl, $(C_{1-6})$alkoxy$(C_{1-6})$alkyl, $(C_{2-6})$alkenyl, amino$(C_{3-10})$alkenyl, hydroxy$(C_{3-10})$alkenyl, halo$(C_{2-6})$alkenyl, cyano$(C_{2-6})$alkenyl, thio$(C_{3-10})$alkenyl, carboxy$(C_{3-10})$alkenyl, 1, aryl$(C_{2-6})$alkenyl, $(C_{2-6})$alkynyl, $(C_{1-6})$heteroalkyl, $(C_{2-6})$heteroalkenyl, $(C_{2-6})$heteroalkynyl, $(C_{1-6})$alkoxy, $(C_{3-10})$alkenyloxy, $(C_{1-6})$alkylenedioxy, amino$(C_{2-6})$alkoxy, hydroxy$(C_{2-6})$alkoxy, halo$(C_{1-6})$alkoxy, cyano$(C_{1-6})$alkoxy, thio$(C_{1-6})$alkoxy, carboxy$(C_{2-6})$alkoxy, aryl$(C_{1-6})$alkoxy, $(C_{1-6})$alkoxy$(C_{2-6})$alkoxy, halo$(C_{1-6})$alkoxy$(C_{2-6})$alkoxy, mono$(C_{1-6})$alkylamino, di$(C_{1-6})$alkylamino, $(C_{1-6})$alkylcarbonylamino, $(C_{2-6})$alkenylcarbonylamino, $(C_{6-14})$arylcarbonylamino, $(C_{1-6})$alkoxycarbonylamino, $(C_{6-10})$aryloxycarbonylamino, $(C_{1-6})$alkylcarbonyl, $(C_{2-6})$alkenylcarbonyl, $(C_{6-10})$arylcarbonyl, $(C_{1-8})$alkoxycarbonyl, $(C_{6-14})$aryloxycarbonyl, $(C_{1-6})$alkylsulfonylamino, $(C_{2-6})$alkenylsulfonylamino and $(C_{6-14})$arylsulfonylamino. In some embodiments, at least one of $R_1$, $R_2$, $R_3$ or $R_4$ is a haloalkyl.

In some embodiments, at least one of $R_1$-$R_4$ can be a mono-haloalkyl, a di-haloalkyl or a tri-haloalkyl. In some embodiments, the haloalkyl can be a bromoalkyl, chloroalkyl, fluoroalkyl or iodoalkyl. In some embodiments, the haloalkyl is a trifluoroalkyl. In some embodiments, the haloalkyl is a trifluoroethyl, trifluoropropyl or trifluorobutyl. In some embodiments, the haloalkyl is a difluoroethyl, difluoropropyl or difluorobutyl.

In some embodiments, X is 1 to 90, 10 to 80 or 20 to 70. In some embodiments, X is 1 to 10, 1 to 5 or 1 to 3. In some embodiments, Y is 1 to 90, 10 to 80 or 20 to 70. In some embodiments, Y is 1 to 10, 1 to 5 or 1 to 3. In some embodiments, Z is 10 to 250, 50 to 200 or 75 to 150. As one of skill in the art would recognize, the values of X and could vary in each Z subunit. Thus, e.g., X could be 3 and Y could be 4 in a first Z subunit, and then X could be 10 and Y could be 2 in a second Z subunit.

In some embodiments, $R_1$ is a trifluoropropyl; $R_2$, $R_3$, and $R_4$ are independently $C_1$-$C_3$ alkyl; $R_5$ is vinyl; X is 1 to 2; Y is 1 to 2; and Z is 100 to 200. In some embodiments, the polysiloxane of the present invention is trifluoropropyl methyldimethyl polysiloxane.

An aperture can be formed into the device matrix by methods known to those in the art. For example, an aperture can be formed by laser drilling, mechanical pressing, or mechanical drilling. Various types of laser drill apparatus can be used. For example, a LPM model laser drill from LasX (Minneapolis, Minn.) or a laser drill manufactured by PRECO Laser Systems (Somerset, Wis.) can be used. In some embodiments, the aperture is formed simultaneously with the matrix, e.g., if the device is farmed by a molding, the matrix is formed in a mold with a molding pin, and when molding pin is removed, an aperture is formed. Likewise, if the device is formed by compression in a mold, the matrix can be compressed around a rod inserted into the mold, and when the rod is removed, an aperture is formed.

In some embodiments, the device comprises a matrix, i.e., the aperture matrix, contained within the one or more apertures of the device. The aperture matrix can be comprised of any material as described above for the device or different material than the device matrix.

In some embodiments, the aperture matrix comprises an active agent. In some embodiments, the active agent is homogeneously dispersed in the aperture matrix. As used herein, "homogeneous" refers to a composition, e.g., the aperture matrix, that has a substantially uniform distribution of ingredients throughout (i.e., an aperture matrix of the present invention does not have a composition gradient, is not multiphasic, or have a multi-laminate structure).

In some embodiments, the active agent is heterogeneously dispersed in the aperture matrix. As used herein, "heterogeneous" refers to a composition, e.g., the aperture matrix, that does not have a substantially uniform distribution of ingredients throughout. Thus, a "heterogeneous mixture" refers to a composition of two or more ingredients, in which the ingredients are not substantially uniformly distributed (i.e., there can be segments, regions, or areas of the mixture with substantially differing amounts of any of the ingredients).

The concentration of the active agent in the aperture matrix can vary, depending on the nature of the active agent, the desired dosage amount, the desired release rate, the nature of the matrix, etc. In some embodiments, the concentration of the active agent in the aperture matrix is greater than or equal to about 80% by weight active agent, greater than or equal to about 60% by weight active agent, greater than or equal to about 50% by weight active agent, greater than or equal to about 40% by weight active agent, or greater than or equal to about 20% by weight active agent. In some embodiments, the concentration of the active agent in the aperture matrix is less than 20% by weight.

In some embodiments, the aperture matrix is in a solid form prior to administration to a female, but transforms into a semi-solid or liquid form after administration to a female, e.g. by increased temperature and/or moisture. Upon transformation into a liquid or semi-solid state, the aperture matrix can be released, either wholly or partly, into the vaginal environment.

The aperture matrix can fill the aperture of the intravaginal device. In some embodiments, the aperture matrix completely fills the volume of the aperture. In some embodiments, the aperture matrix fills greater than 20%, greater than 40%, greater than 50%, greater than 70%, or greater than 90% of the volume of the aperture. One of skill in the art will understand that the term "aperture" refers to the void of the intravaginal device prior to addition of the aperture matrix to fill the void.

In some embodiments, the active agent does not interact or form complexes with the aperture matrix. In some embodiments, the aperture matrix can be chosen due to its mechanical and physical properties (e.g., solubility of an active agent in the material). In some embodiments, a cap covers the aperture matrix. The cap can be removed prior to use of the intravaginal device. The cap can function to contain the aperture matrix and prevent any leakages of material therefrom. The cap can impede the diffusion of active agent from the aperture matrix until administration.

As used herein, an "active agent" refers to a drug, protein, hormone, vitamin, nutritional supplement, or any other substance intended for use in the treatment, mitigation, cure or prevention of a disease or any other medical condition. In some embodiments, an active agent can be administered to a subject to treat a condition or a symptom thereof in a subject. For example, in some embodiments, an active agent is a component in a medicinal compound administered to treat one or more conditions, or the symptoms thereof, in a subject.

The intravaginal device of the present invention can be used to deliver one or more active agents. Active agents suitable for use with the present invention can have a localized effect and/or as a systemic effect. Active agents suitable for use with the present invention include, but are not limited to, an analgesic, an anti-inflammatory agent, an anti-microbial agent, an anesthetic, an anti-osteoporosis agent, an anticholinergic agent, a steroid hormone, and combinations thereof.

In some embodiments, the active agent is a steroid hormone, an anticholinergic, an anesthetic, combinations thereof, or derivatives thereof. A steroid hormone can include, for example, an estrogen, a progestin, a progesterone, a testosterone, derivatives thereof, or combinations thereof.

As used herein, an "estrogen" refers to any of various natural or synthetic compounds that stimulate the development of female secondary sex characteristics and promote the growth and maintenance of the female reproductive system, or any other compound that mimics the physiological effect of natural estrogens. Estrogens suitable for use with the present invention also include compounds that can be converted to active estrogenic compounds in the uterine environment. For example, in some embodiments, a conjugated estrogen can be administered from an intravaginal device of the present invention. As used herein, the term "conjugated" refers to the sulfate ester, glucuronide ester, or mixed sulfate-glucuronide esters, of an estrogen. Estrogens suitable for use with the present invention also include pharmaceutically suitable salt forms of estrogens. In some embodiments, the salt can be a sodium, potassium, or 2-amino-2-(hydroxymethyl)-1,3-propanediol (Tris) salt. In some embodiments, an estrogen suitable for use with the present invention can be useful for Hormone Replacement Therapy (HRT) regimens. In some embodiments, an estrogen suitable for use with the present invention can be useful for the treatment of osteoporosis in a subject in need thereof. In some embodiments, an estrogen suitable for use with the present invention can be useful as a contraceptive agent.

Estrogens suitable for use in the present invention include, but are not limited to, natural and synthetic compounds having estrogenic activity, such as, for example, estradiol (17β-estradiol), 17α-estradiol, estriol, estrone, and their esters, such as the acetate, sulfate, valerate or benzoate esters of these compounds, including, for example, estradiol 17β-cypionate, estradiol 17-propionate, estradiol 3-benzoate, and piperazine estrone sulfate; ethinyl estradiol; conjugated estrogens (natural and synthetic); agonistic anti-estrogens; and selective estrogen receptor modulators.

Prodrugs of suitable estrogens can also be used in the device of the present invention. As used herein, a "prodrug" denotes a derivative of a known direct acting drug, which derivative has enhanced delivery characteristics and therapeutic value as compared to the drug and is transformed into the active drug by an enzymatic or chemical process. Examples of estrogen prodrugs include, but are not limited to, estradiol acetate (which is converted in vivo to 17β-estradiol) and mestranol (which is converted in vivo to ethinyl estradiol). In some embodiments, the estrogen is estradiol, estriol, mestranol, ethinyl estradiol, diethylstilbestrol, or combinations thereof.

As used herein, a "progestin" refers to a progestogen, a progestational substance, or any pharmaceutically acceptable substance in the steroid art that generally possesses progestational activity including synthetic steroids that have progestational activity. Progestins suitable for use with the present invention can be of natural or synthetic origin. Progestins generally possess a cyclo-pentanophertanthrene nucleus. In some embodiments, a progestin suitable for use with the present invention can be useful for Hormone Replacement Therapy (HRT) regimens. In some embodiments, a progestin suitable for use with the present invention can be useful as a contraceptive agent.

Progestins suitable for use in the present invention include, but are not limited to, natural and synthetic compounds having progestational activity, such as, for example, progesterone, medroxyprogesterone, medroxyprogesterone acetate, chlormadinone acetate, norethindrone, cyproterone acetate, norethindrone acetate, desogestrel, levonorgestrel, drospirenone, trimegestone, norgestrel, norgestimate, norelgestromin, etonogestrel, dienogest, gestodene, megestrol, and other natural and/or synthetic gestagens. In some embodiments, the progestin is progesterone, etonogestrel, levonorgestrel, gestodene, norethisterone, drospirenone, or combinations thereof.

Prodrugs of suitable progestins can also be used in the intravaginal device of the present invention. Ethynodiol diacetate, which is converted in vivo to norethindrone, is an example of a progestin prodrug that can be used in the present invention. Additional examples of progestin prodrugs include, but are not limited to, norgestimate (which is converted in vivo to 17-deacetyl norgestimate, also known as norelgestromin), desogestrel (which is converted in vivo to 3-keto desogestrel, also known as etonogestrel), and norethindrone acetate (which is converted in vivo to norethindrone).

In some embodiments, the progestin is desogestrel, etonogestrel, norgestimate, or combinations thereof.

In some embodiments, the active agent is a modified testosterone, e.g., a derivative of the synthetic steroid ethisterone. In some embodiments, the modified testosterone is danazol.

In some embodiments, the intravaginal device of the present invention contains two active agents, such as a progestin and an estrogen. In some embodiments, the intravaginal device contains etonogestrel and ethinyl estradiol. In some embodiments, a combination of a progestin and an estrogen suitable for use with the present invention can be useful for contraceptive regimens.

In some embodiments, two or more active agents are dispersed together in the aperture matrix. In some embodiments, two or more active agents are dispersed in separate locations in the aperture matrix.

As used herein, an "anesthetic" is a compound that blocks the passage of pain impulses in nerve pathways to the brain and induces a loss of sensation in one or more areas of the body without loss of vital functions. Particular examples of such anesthetic agents include, but are not limited to, bupivacaine, ropivacaine, dibucaine, procaine, chioroprocaine, prilocaine, mepivacaine, etidocaine, tetracaine, lidocaine, benzocaine, articaine, benoxinate, naepaine, piperocaine, tetracaine, and combinations thereof. In some embodiments, the anesthetic is lidocaine or tetracaine.

As used herein, an "anticholinergic" is a compound that blocks the neurotransmitter acetylcholine in the central and the peripheral nervous system. Anticholinergics for use with the present invention include, but are not limited to, oxybutynin, bethanechol, propiverine, propantheline, methylbenactyzium, scopolamine, tolterodine, trospium, combinations thereof, and salts thereof. In some embodiments, the anticholinergic is oxybutynin or a salt thereof. In some embodiments, the anticholinergic is oxybutynin hydrochloride.

In some embodiments, the intravaginal device of the present invention further comprises an excipient. As used herein, an "excipient" refers to a substance that is used in the formulation of pharmaceutical compositions, and, by itself, generally has little or no therapeutic value. One of skill in the art will recognize that a wide variety of pharmaceutically acceptable excipients can be used with the present invention including those listed in the *Handbook of Pharmaceutical Excipients*, Pharmaceutical Press 4th Ed. (2003) and *Remington The Science and Practice of Pharmacy*, Lippincott Williams & Wilkins, 21st Ed. (2005), which are incorporated herein by reference in their entirety. As used herein, the term "pharmaceutically acceptable" refers to those compounds, materials, and/or compositions which are, within the scope of sound medical judgment, suitable for contact with the tissues of human beings and animals without excessive toxicity, imitation, allergic response, or other possible complications commensurate with a reasonable benefit/risk ratio. In some embodiments, the excipient is present in the device matrix, the aperture matrix, or both.

In some embodiments, the matrix of the intravaginal device of the present invention controls the rate of release of an active agent contained therein. As used herein, the "rate of release" or "release rate" refers to an amount or concentration of active agent that is released from the device over a defined period of time.

In some embodiments, the material of the intravaginal device, i.e., the device matrix, is permeable to an active agent in the aperture matrix. In some embodiments, the device matrix is impermeable to the active agent, but the aperture matrix is permeable to the active agents. The device matrix can be used to control the rate of release of an active agent from the intravaginal device of the present invention. For example, if the intravaginal device matrix is a polymer, the rate of release of an active agent from the device can be controlled by controlling the degree of cross-linking present in the polymer, A high degree of cross-linking would be expected to result in a lower rate of release of the active agent from the polymer. The degree of crosslinking can be controlled by the amount of crosslinker or catalyst used during production of the intravaginal device. See, e.g., U.S. Pat. No. 6,394,094. In some embodiments, permeation enhancers can be added to the polymer to increase the rate of release of the active agent from the polymer. The rate of release of an active agent can also be controlled or modulated by the addition to the polymer matrix of additional agents or excipients, such as, for example, mineral oil, or fatty acid esters.

The amount and rate of active agent released from the device can be determined by those of skill in the art and is dependent on many factors, e.g., the active agent, the condition to be treated, the age and/or weight of the subject to be treated, etc. For example, the release rate can be measured in vitro using, e.g., the USP Apparatus Paddle 2 method. The device can be placed into a 500 ml solution of 0.05 M SDS at 37° C. with a paddle speed of 50 rpm. The amount of active agent diffused into solution can be assayed by methods known in the art, e.g., by HPLC. In some embodiments, the active agent is released from the device at an average rate of about 0.01 mg to about 10 mg per 24 hours in situ, or about 0.05 mg to about 5 mg per 24 hours in situ, or about 0.1 mg to about 1 mg per 24 hours in situ. In some embodiments, the active agent is released from the device at an average rate of about 1 mg to about 100 mg per 24 hours in situ or about 5 mg to about 50 mg per 24 hours in situ. Alternatively, the release rate of the active agent from the device can be measured in viva by monitoring blood levels in a subject which has been administered the intravaginal device containing the active agent.

In some embodiments, two or more active agents can be released from the device at a different rate per 24 hours in situ. For example, an estrogen can be released from the device at an average rate of about 0.01 mg to about 0.1 mg per 24 hours in situ and a progestin can be released from the device at an average rate of about 0.08 mg to about 0.2 mg per 24 hours in situ, or an estrogen can be released from the device at an average rate of about 0.1 mg to about 1 mg per 24 hours in situ and a progestin can be released from the device at an average rate of about 0.05 mg to about 5 mg per 24 hours in situ, or an estrogen can be released from the device at an average rate of about 0.05 mg to about 5 mg per 24 hours in situ and a progestin can be released from the device at an average rate of about 1 mg to about 100 mg per 24 hours in situ.

Various durations of administration can be used with the intravaginal device of the present invention. For example, in some embodiments, a longer duration of administration is needed, e.g. with chronic conditions or birth control. In some embodiments of the present invention, an active agent is released from the intravaginal device at a steady rate for at least about 6 months after administration to a female, for up to at least about 1 month or about 30 days after administration to a female, for at least about 25 days after administration to a female, for at least about 21 days after administration to a female, for at least about 15 days after administration to a female, for at least about 10 days after administration to a female, for at least about 7 days after administration to a female, or for at least about 4 days after administration to a female.

As used herein, a "steady rate" is a release rate that does not vary by an amount greater than 70% of the amount of active agent released per 24 hours in situ, by an amount greater than 60% of the amount of active agent released per 24 hours in situ, by an amount greater than 50% of the amount of active agent released per 24 hours in situ, by an amount greater than 40% of the amount of active agent released per 24 hours in situ, by an amount greater than 30% of the amount of active agent released per 24 hours in situ, by an amount greater than 20% of the amount of active agent released per 24 hours in situ, by an amount greater than 10% of the amount of active agent released per 24 hours in situ, or by an amount greater than 5% of the amount of active agent released per 24 hours in situ.

In some embodiments, the active agent is a progestin with a steady release rate of active agent in situ of about 80 µg to about 200 µg per 24 hours, about 90 µg to about 150 µg per 24 hours, about 90 µg to about 125 µg per 24 hours, or about 95 µg to about 120 µg per 24 hours.

In some embodiments, the active agent is an estrogen with a steady release rate of active agent in situ of about 10 µg to about 100 µg per 24 hours, about 10 µg to about 80 µg per 24 hours, about 10 µg to about 60 µg per 24 hours, about 10 µg to about 40 µg per 24 hours, about 10 µg to about 20 µg per 24 hours, or about 10 µg to about 15 µg per 24 hours.

In some embodiments, more rapid delivery of the active agent is desired, e.g. for an anesthetic, anti-inflammatory, and/or anti-microbial. Thus, in some embodiments, the active agent is released from the intravaginal device for about 15 minutes to about 1 day, about 10 minutes to about 12 hours, about 30 minutes to about 6 hours, or about 1 hour to about 3 hours. In some embodiments, various concentrations of active agent are present in the intravaginal device of the present invention. In some embodiments, an active agent is supersaturated in the matrix at 25° C. As used herein, "supersaturated" can refer to the amount of an active agent that is about one to about five times the amount necessary to obtain the saturation concentration of the active agent in the matrix at 25° C.

Figure 5:
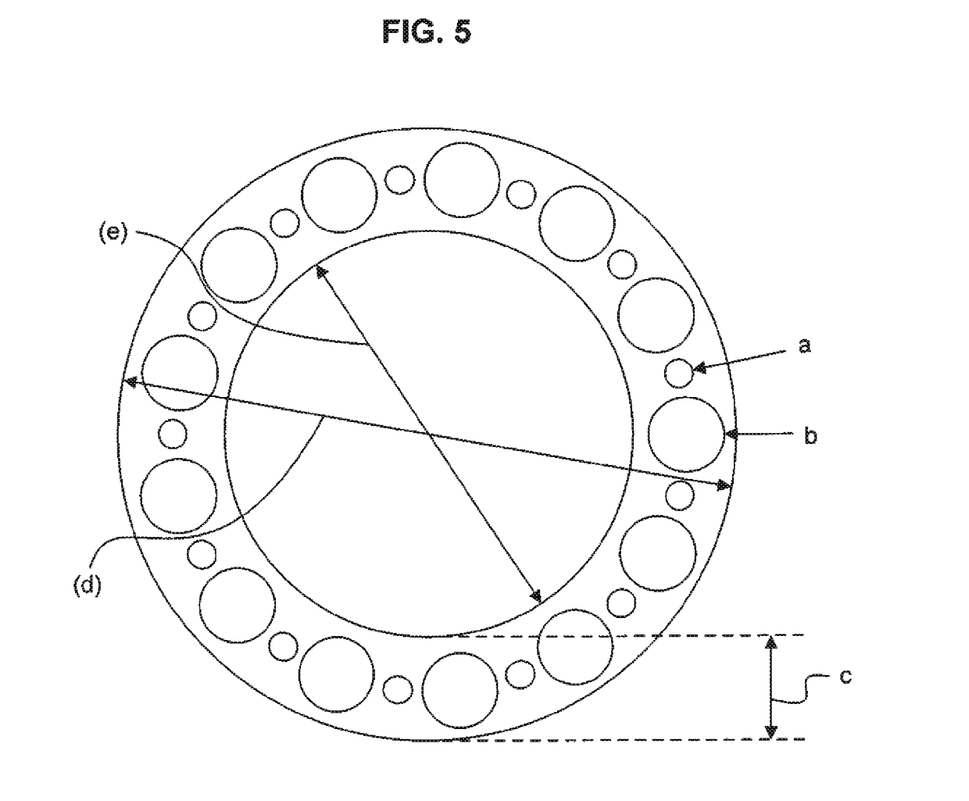
FIG. 5 depicts a top down view of an exemplary intravaginal device of the present invention with (a) 13 apertures, each aperture having an exterior entry diameter of 2.5 mm, and (b) an ejector pin pad in between each aperture; the diameter of each ejector pin pad being 7.0 mm. The device has a cross sectional diameter (c) of 9.5 mm, an outer diameter (d) of 57 mm, and an inner diameter (e) of 38 mm.

The device of the present invention can be any size suitable for placement in a vaginal tract. In some embodiments, the device has an outer diameter of about 20 mm to about 100 mm, about 30 mm to about 80 mm, about 40 mm to about 70 mm, about 45 mm to about 65 mm, or about 50 mm to about 60 mm. As used herein, an "outer diameter" refers to any straight line segment that passes through the center of the device and whose endpoints are on the outer perimeter of the device. See FIG. 5(d). In some embodiments, the outer diameter is the longest straight line segment that passes through the center of the device and whose endpoints are on the outer perimeter of the device.

In some embodiments, the device has an inner diameter of about 10 mm to about 60 mm, about 10 mm to about 50 mm, about 10 mm to about 40 mm, about 20 mm to about 40 mm, about 10 mm to about 30 mm, or about 30 mm to about 50 mm. As used herein, an "inner diameter" of the device refers to any straight line segment that passes through the center of the device and whose endpoints are on the inner perimeter of the device. See FIG. 5(e). In some embodiments, the inner diameter of the device is the longest straight line segment that passes through the center of the device and whose endpoints are on the inner perimeter of the device.

In some embodiments, the device has a cross-sectional diameter of about 1 mm to about 10 mm, about 1 mm to about 8 mm, about 1 mm to about 5 mm, about 2 mm to about 7 mm, about 3 mm to about 7 mm, about 4 mm to about 6.5 mm, or about 5 mm to about 6 mm. In some embodiments, the device has a cross-sectional diameter of about 3 mm to about 10 mm, about 5 mm to about 10 mm, about 6 mm to about 9 mm, or about 7 mm to about 9 mm. As used herein, a "cross-sectional diameter" refers to the longest straight line segment that passes through the center of the cross section of the device and whose endpoints are on the outer perimeter of the cross-section device. See FIG. 5(c).

The intravaginal device of the present invention can be in various shapes and sizes, thereby producing a device with various surface areas. As used herein, "surface area" refers to the total area of the device that is exposed to the environment, e.g., to the vagina, cervix, or uterus of a female. In some embodiments, the device has a surface area of about 800 mm$^2$ to about 2000 mm$^2$, about 1000 mm$^2$ to about 2000 mm$^2$, about 1200 mm$^2$ to about 2000 mm$^2$, about 1400 mm$^2$ to about 2000 mm$^2$, or about 1600 mm$^2$ to about 2000 mm$^2$.

Methods of Making the Intravaginal Device

Various methods can be used to make the intravaginal devices of the present invention. Various means of producing intravaginal devices are known in the art. See, e.g., U.S. Pat. Nos. 6,544,546; 6,394,094; and 4,155,991. The present invention is directed to a method of making an annular intravaginal device, the method comprising (i) forming the intravaginal device by molding or compressing a device matrix, wherein an aperture is formed simultaneously with the molding or compressing of the device matrix a non-porous polymeric material, and (b) forming an aperture in the ring.

In some embodiments, the invention is related to a method of making an annular intravaginal device, the method comprising: (i) forming the intravaginal device by molding or compressing a device matrix, in a mold, wherein an aperture is formed simultaneously with the molding or compressing of the device matrix, the aperture extending into the device and having: (a) an interior diameter, and (b) an exterior entry diameter, wherein the exterior entry diameter of the aperture is less than the interior diameter of the aperture, and (ii) placing an aperture matrix inside the aperture of the device matrix. In some embodiments, the aperture matrix is in a non-solid state when placed in the aperture, and then solidifies after placement in the aperture.

The present invention is also directed to an intravaginal device made by this method. In some embodiments, the device matrix is in a liquid state prior to being molded or compressed. In some embodiments, the liquid matrix solidifies upon cooling or polymerizing. In some embodiments, the matrix in a liquid state solidifies with the addition of a catalyst. In some embodiments, the aperture is formed simultaneously due to the presence of a rod or pin in the mold, and the aperture is formed upon removal of the rod or pin.

In some embodiments, compression molding is used to form the device of the present invention. In some embodiments, compressing a substantially homogeneous mixture to form a compressed matrix can be achieved by compression molding, or alternatively, by the use of a die press. As used herein, "compressed" refers to a mixture that has been compacted or fused under pressure. A compressed mixture has a density that is greater than the mixture prior to compression. Compressed devices are known to those in the art. See, e.g., U.S. Pat. Pub. No. 2007/0254014 A1.

In some embodiments, ejector pins are used to remove the device from the mold. Ejector pin pads can be flat surfaces on the intravaginal device which aid in removal of the intravaginal device from the mold, e.g., to aid in separating the device from the rods used to form the apertures. In some embodiments, the ejector pin pads can be located in between the apertures on the device.

Substantially homogeneous mixtures uses with some embodiments of the present invention can be prepared using a wide variety of methods for mixing the ingredients, including any method recognized by artisans skilled in the methods of mixing ingredients, that results in a substantially homogeneous mixture suitable for compressing.

In some embodiments, the method of the present invention further comprises curing the compressed intravaginal device. As used herein, "curing" refers to a process useful to solidify, harden, or cross-link a substantially homogeneous compressed composition of the present invention. Curing can comprise heating, drying, crystallizing, cross-linking, photo-curing (e.g., exposing to monochromatic or broad-band ultraviolet, visible, or infrared light) or combinations thereof.

Methods of Treatment

As used herein, "female" refers to any animal classified as a mammal, including humans and non-humans, such as, but not limited to, domestic and farm animals, zoo animals, sports animals and pets. In some embodiments, female refers to a human female.

As used herein, the term "administering to" refers to placing an intravaginal device of the present invention in contact with the vaginal and/or urogenital tract of a female.

The terms "treat" and "treatment" refer to both therapeutic treatment and prophylactic, maintenance, or preventative measures, wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms or signs; diminishment of extent of condition, disorder or disease; stabilization (i.e., not worsening) of the state of condition, disorder or disease; delay in onset or slowing of condition, disorder or disease progression; amelioration of the condition, disorder or disease state, remission (whether partial or total), whether detectable or undetectable; or enhancement or improvement of condition, disorder or disease. Treatment includes eliciting a clinically significant response, without excessive levels of side effects.

In some embodiments, the present invention can be directed to a method of site specific drug delivery to the vaginal and/or urogenital tract, and the treatment of any disease in which the active agent can be absorbed in the vaginal and/or urogenital tract. In some embodiments, the intravaginal device of the present invention can be administered alone or in conjunction with other medications or pharmaceutical compositions.

An intravaginal device of the present invention contains a therapeutically effective amount of active agent. The term "therapeutically effective amount" refers to an amount of active agent that diminishes one or more symptoms of a disease or disorder (i.e., treats a disease or disorder) in a subject. In some embodiments, the term "therapeutically effective amount" refers to an amount of active agent sufficient to achieve a desired physiologic state, e.g., the anesthetizing of all or part of the vaginal tract. The precise therapeutic dosage of an active agent necessary to be therapeutically effective can vary between subjects (e.g., due to age, body weight, condition of the subject, the nature and severity of the disorder or disease to be treated, and the like). In some embodiments, the term "therapeutically effective amount" refers to an amount of active agent sufficient to achieve a desired physiological state, e.g., anesthetizing all or part of the vaginal tract. For example, the phrase "therapeutically effective amount" when referring to an anesthetic can refer to an amount sufficient to reduce pain by at least about 15 percent, by at least 50 percent, by at least 90 percent. In some embodiments, the therapeutically effective amount is sufficient to prevent a clinically significant pain for a subject. As used herein, the term "anesthesia" refers to the condition of, e.g., a local numbness and/or analgesia and/or inhibitory effects on sensory and motor function, induced, by way of contact with an anesthetic agent described herein.

In some embodiments, the therapeutically effective amount cannot be specified in advance and can be determined by a caregiver, for example, by a physician or other healthcare provider, using various means, for example, dose titration. Appropriate therapeutically effective amounts can also be determined by routine experimentation using, for example, animal models.

In some embodiments, the intravaginal device can be used as a method of providing contraception to a female for the treatment of a condition or disorder, or as a method of providing contraception and treating a condition or disorder in a female. Such conditions and disorders include, but are not limited to breakthrough bleeding; irregular withdrawal bleeding; menstrual bleeding disorders; symptoms associated with an ovarian cyst, uterine leiomyoma (fibroid tumor), and/or polycystic ovarian syndrome; hirsutism; iron deficiency anemia; menstrual disorders; acne; endometriosis; endometrial cancer, ovarian cancer; benign breast disease; infections; ectopic pregnancy; temporomandibular disorder; catamenial symptoms; non-menstrual related headache, nausea, and/or depression; peri-menopausal symptoms; hypoestrogenism; menopausal disorders; and loss of bone density. Thus, in some embodiments, the method of contraception comprises administering to a female in need thereof an intravaginal device comprising: (a) an aperture extending into the device, the aperture having: (i) an interior diameter; and (ii) an exterior entry diameter, wherein the exterior entry diameter of the aperture is less than the interior diameter of the aperture, and (b) an aperture matrix contained within the aperture, wherein the aperture matrix comprises an estrogen and a progestin in an amount sufficient to provide contraception.

In some embodiments, an intravaginal device of the present invention can be administered to provide contraception and treat a condition or disorder in a female, wherein the female is in need of both contraception and treatment of the condition or disorder. The female can be, for example, of childbearing age or peri-menopausal.

As used herein, a "peri-menopausal female" refers to a woman who has not yet definitely arrived at menopause but who is experiencing symptoms associated with menopause. "Peri-menopause" means "about or around the time of menopause" and encompasses the years preceding the last menstrual period during which ovarian function declines and ultimately ceases and can include the presence of symptoms and irregular cycles. As used herein, a "menopausal female" refers to a woman who has definitely arrived at menopause and may be experiencing symptoms associated with menopause. Menopause or post-menopause is the permanent cessation of menstruation after the loss of ovarian activity and is generally defined clinically as the absence of menstruation for about one year. Menopause may occur naturally in a woman or it may be artificially induced, e.g., through surgical or chemical means. For example, removal of the ovaries, which can occur, e.g., through hysterectomy, frequently leads to symptoms associated with menopause.

In some embodiments, an intravaginal device of the present invention can be administered to a subject to treat a menopausal condition. As used herein, a "menopausal condition" refers to a condition associated with menopause, or the period of natural cessation of menstruation. Additionally, the term "menopausal condition" can relate to a condition related to peri-menopause, post-menopause, or cophorectomized women, or women whose endogenous sex hormone production has been suppressed by a pharmaceutical chemical composition, e.g., a GnRH agonist such as leuprolide-acetate sold under the trademark LUPRONE® (TAP Pharmaceutical Products, Inc., Lake Forest, Ill.) or goserelin acetate, sold under the trademark ZOLADEX® (AstraZeneca Pharmaceuticals, Wilmington, Del.). Thus, in some embodiments, the method of hormone replacement therapy comprises administering to a female in need thereof an intravaginal device comprising: (a) an aperture extending into the device, the aperture having: (i) an interior diameter; and (ii) an exterior entry diameter, wherein the exterior entry diameter of the aperture is less than the interior diameter of the aperture, and (b) an aperture matrix contained within the aperture, wherein the aperture matrix comprises an estrogen in an amount sufficient to provide, relief from symptoms associated with menopause or peri-menopause.

Various menopausal conditions are known in the art. Menopausal conditions include, but are not limited to, hot flashes, vaginal dryness, pain during intercourse, increased risk of infection, inability to control urination (e.g., urinary incontinence), increased frequency of urinary infection, vaginal atrophy, kraurosis vulvae, hot flashes and/or night sweats, fatigue, emotional changes (e.g., mood swings and changes in sexual interest), sleep disturbances (e.g., insomnia), dry skin and hair, increased growth of facial and body hair, increased risk of heart disease, aches and pains in the joints, headaches, palpitations (i.e., rapid, irregular heart beats), vaginal itching, osteoporosis, osteopenia, and generalized itching.

In some embodiments, an intravaginal device of the present invention can be administered to a subject to treat osteoporosis. As used herein, "osteoporosis" refers to a condition characterized by a decrease in bone mass and density, causing bones to become fragile. In some embodiments, osteoporotic conditions include increased risk of fracture, especially fractures of the hip or spine. In some embodiments, the method of treating osteoporosis comprises administering to a female in need thereof an Intravaginal device comprising: (a) an aperture extending into the device, the aperture having: (i) an interior diameter; and (ii) an exterior entry diameter, wherein the exterior entry diameter of the aperture is less than the interior diameter of the aperture, and (b) an aperture matrix contained within the aperture, wherein the aperture matrix comprises an estrogen in an amount sufficient to provide relief from symptoms associated with osteoporosis.

In some embodiments, an intravaginal device of the present invention can be administered to a subject to treat urinary incontinence. As used herein, "urinary incontinence" refers to the complete or partial loss of bladder control, resulting in frequent urination and/or uncontrolled urination. In some embodiments, the treatment of urinary incontinence comprises administering to a female in need thereof an intravaginal device comprising: (a) an aperture extending into the device, the aperture having: (i) an interior diameter; and (ii) an exterior entry diameter, wherein the exterior entry diameter of the aperture is less than the interior diameter of the aperture, and (b) an aperture matrix contained within the aperture, wherein the aperture matrix comprises an anticholinergic in an amount sufficient to provide relief from symptoms associated with urinary incontinence.

In some embodiments, an intravaginal device of the present invention can be administered to a subject to treat vaginal infection. As used herein, "vaginal infection" refers to a bacterial or viral infection in or around the vagina, cervix, or uterus. Symptoms of vaginal infection include, but are not limited to, itching, burning, soreness, pain during intercourse and/or urination, and can be accompanied by vaginal discharge.

In some embodiments, an intravaginal device of the present invention can be administered to a subject to treat vaginal pain. As used herein, "vaginal pain" refers to pain localized in the female reproductive tract, e.g., the vagina, cervix, or uterus, and combinations thereof. The pain can be due to a medical condition and/or psychological difficulties. Medical conditions can include chronic diseases, minor ailments, and medications. Psychological causes can be related to physical or sexual abuse. As used herein, "abdominal pain" refers to pain in the region of the stomach, small intestine, large intestine, or bowel. In some embodiments, the intravaginal device of the present invention can be administered to a subject to anesthetize the subject, or locally anesthetize all or part of the female reproductive tract.

In some embodiments, the intravaginal device of the present invention can deliver an anesthetic agent locally to the cervical region in the female to induce anesthesia temporarily to the cervical region. For example, the intravaginal device can be used for locally delivering and immediately releasing an anesthetic agent to the cervical region of a female. The device can be inserted into the vaginal canal of the female, and be retained therein temporarily. Upon the insertion of the ring into the vaginal canal, the anesthetic agent is immediately released from the device, and induces temporary anesthesia in the cervical region. This can be beneficial, e.g., during a gynecological procedure, wherein the pain and discomfort associated with the procedure can be avoided. Thus, in some embodiments, the method for anesthetizing the cervical region of a female in need thereof comprises: (a) administering to the vaginal canal of a female an intravaginal device comprising: (i) an aperture extending into the device, the aperture having: (1) an interior diameter; and (2) exterior entry diameter, wherein the exterior entry diameter of the aperture is less than the interior diameter of the aperture, and (ii) an aperture matrix contained within the aperture, wherein the aperture matrix comprises an anesthetic in an amount sufficient to anesthetize the cervical region, and (b) removing the intravaginal ring from the vaginal canal after induction of the anesthesia of the cervical region.

In some embodiments, an intravaginal device of the present invention can be administered to a subject to treat inflammation. As used herein, "inflammation" refers to the body's natural response to injury or infection, in which the site of injury or infection might display various degrees of pain, swelling, heat, redness and/or loss of function.

EXAMPLES

Example 1

The device matrix of an intravaginal ring is prepared by mixing silicone polymer with a catalyst, e.g., methyl chloride, to start the polymerization process. The catalyzed mixture is added to a mold, the mixture encompassing the mold. Thirteen apertures in the vaginal ring are formed by the replacement of rods in the mold prior to polymerization and curing. The rods are shaped such that an aperture having an exterior entry diameter smaller than the interior diameter is achieved after the device is compressed and the rods are removed. The molded mixture is then cured in a Grieve oven (Grieve Corp., Round Lake, Ill.) at about 90° C. for about six hours, forming an intravaginal ring having a silicone matrix. The process yields an intravaginal ring having an outer diameter of about 55 mm, an inner diameter of about 38 mm and a cross-sectional diameter of about 8 mm. The exterior entry diameter is 4 mm, the interior diameter is 6 mm, and the length of the aperture is 6 mm. The resulting intravaginal ring is referred to as the template ring.

Example 2

An aperture matrix containing estrogen and progestin is prepared by forming a homogeneous mixture of an estrogen, a progestin, and a silicone elastomer and placing the ingredients in a Ross DPM-4 mixer (Ross double planetary mixer and dispenser supplied by Charles Ross & Son, Hauppauge, N.Y.), where the ingredients are mixed and degassed under vacuum for about 30 minutes or until the estrogen and progestin are distributed homogeneously throughout the polymer matrix. This mixture is then mixed with a catalyst and poured into each of the apertures of the template ring of Example 1. The aperture matrix is allowed to cure.

The mold is disassembled and the n ejected using an ejector pin. The ring is packaged in a heat sealed foil pouch.

Example 3

An aperture matrix containing lidocaine is prepared by (1) mixing "Gelucire 44/14" lauroyl macrogolglyceride (Gattefosse' S. A., Saint-Priest Cedex, France) (40% by weight) with lidocaine (60% by weight), or (2) mixing "Gelucire 50/13" stearoyl macrogolglyceride (Gattefosse' S. A., Saint-Priest Cedex, France) (40% by weight) with lidocaine (60% by weight). The resulting aperture matrix is placed into each of the apertures of the template device of Example 1.

Example 4

An aperture matrix containing lidocaine is prepared by (1) mixing "PLURONIC F38" polyoxypropylene-polyoxyethylene block copolymer surfactant (BASF Corp., Mt. Olive, N.J.) (40% by weight) with lidocaine (60% by weight), or (2) mixing "ABIL 88843" polyethersiloxane emulsifier (Goldschmidt Chemical Corp, Hopewell Va.) (20% by weight), "NATROSOL" hydroxyethylcellulose (20% by weight) and lidocaine (60% by weight). The resulting aperture matrix is placed into each of the apertures of the template device of Example 1.

Example 5

An aperture matrix containing estrogen and progestin is prepared by forming a homogeneous mixture of an estrogen, a progestin, and a trifluoropropyl methyldimethyl polysilicone elastomer and placing the ingredients in a Ross DPM-4 mixer (Ross double planetary mixer and dispenser supplied by Charles Ross & Son, Hauppauge, N.Y.), where the ingredients are mixed and degassed under vacuum for about 30 minutes or until the estrogen and progestin are distributed homogeneously throughout the polymer matrix. This mixture is then mixed with a catalyst and poured into each of the apertures of the template ring of Example 1. The aperture matrix is allowed to cure.

CONCLUSION

All of the various embodiments or options described herein can be combined in any and all variations. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. An annular intravaginal device comprising an aperture extending into the device, the aperture having:
   a. an interior diameter; and
   b. an exterior entry diameter,
   wherein the exterior entry diameter of the aperture is less than the interior diameter of the aperture,
   wherein the aperture extends completely through the device, thereby forming a first exterior entry diameter, an interior diameter, and a second exterior entry diameter,
   wherein the second exterior entry diameter of the aperture is greater than the first exterior entry diameter of the aperture.

2. An annular intravaginal device comprising an aperture extending into the device, the aperture having:
   a. an interior diameter; and
   b. an exterior entry diameter,
   wherein the exterior entry diameter of the aperture is less than the interior diameter of the aperture,
   wherein the aperture extends completely through the device, thereby forming a first exterior entry diameter, an interior diameter, and a second exterior entry diameter,
   wherein the second exterior entry diameter of the aperture is less than the first exterior entry diameter of the aperture.

3. An annular intravaginal device comprising an aperture extending into the device, the aperture having:
   a. an interior diameter; and
   b. an exterior entry diameter,
   wherein the exterior entry diameter of the aperture is less than the interior diameter of the aperture,
   wherein the exterior entry diameter of the aperture is about 10% smaller than the interior diameter of the aperture.

4. An annular intravaginal device comprising an aperture extending into the device, the aperture having:
   a. an interior diameter; and
   b. an exterior entry diameter,
   wherein the exterior entry diameter of the aperture is less than the interior diameter of the aperture,
   wherein the exterior entry diameter of the aperture is about 50% smaller than the interior diameter of the aperture.

* * * * *